United States Patent [19]
Sinta et al.

[11] Patent Number: 5,731,364
[45] Date of Patent: Mar. 24, 1998

[54] PHOTOIMAGEABLE COMPOSITIONS COMPRISING MULTIPLE ARYLSULFONIUM PHOTOACTIVE COMPOUNDS

[75] Inventors: Roger F. Sinta, Woburn; James F. Cameron, Brighton; Timothy G. Adams, Sudbury; Martha M. Rajaratnam, Dedham; Michael F. Cronin, Franklin, all of Mass.

[73] Assignee: Shipley Company, L.L.C., Marlborough, Mass.

[21] Appl. No.: 590,785

[22] Filed: Jan. 24, 1996

[51] Int. Cl.⁶ .................... C08F 2/50; G03F 7/004
[52] U.S. Cl. .................. 522/31; 522/154; 522/25; 427/510; 430/270.1
[58] Field of Search .................. 522/31, 25, 154; 430/270.1; 427/510

[56] References Cited

U.S. PATENT DOCUMENTS

| | | | |
|---|---|---|---|
| 4,450,360 | 5/1984 | Crivello et al. | 260/440 |
| 4,689,289 | 8/1987 | Crivello | 522/31 |
| 4,821,050 | 4/1989 | Yabe et al. | 522/31 |
| 5,089,374 | 2/1992 | Saeva | 522/31 |
| 5,318,876 | 6/1994 | Schwalm et al. | 522/31 |

FOREIGN PATENT DOCUMENTS 0 615 163 A1  9/1994  European Pat. Off. .

OTHER PUBLICATIONS

Watt et al, "A Novel Photoinitiator of Cationic Polymerization: Preparation and Characterization of Bis[4–(diphenylsulfonio)phenyl]sulfide–Bis–Hexafluorophosphate", Journal of Polymer Science: Polymer Chemistry Edition. vol. 22, 1789–1796, 1984.

*Primary Examiner*—Susan W. Berman
*Attorney, Agent, or Firm*—Robert L. Goldberg

[57] ABSTRACT

The invention provides positive- and negative-acting a photoresist compositions that contain a photoacid generator component that includes multiple aryl sulfonium compounds. Specifically, the photoactive component contains at least one multiple cation aryl sulfonium compound, preferably a di-cation compound. The photoactive component of the resists of the invention can be conveniently prepared and provide a deep UV sensitive resist with excellent microlithographic properties.

24 Claims, No Drawings

PHOTOIMAGEABLE COMPOSITIONS COMPRISING MULTIPLE ARYLSULFONIUM PHOTOACTIVE COMPOUNDS

BACKGROUND OF THE INVENTION

1. Field of the Invention

This invention relates to new photoimageable compositions that contain multiple arylsulfonium photoactive compounds. Compositions of the invention are highly useful as deep U.V. (ultraviolet) photoresists with the capability of forming highly resolved features of submicron dimensions.

2. Background

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate. A relief image is provided by development of the latent image pattern in the resist coating. The use of photoresists is generally described, for example, by Deforest, Photoresist Materials and Processes, McGraw Hill Book Company, New York (1975), and by Moreau, Semiconductor Lithography, Principals, Practices and Materials, Plenum Press, New York (1988).

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. No. 4,450,360 and European Application 615163.

Relatively recently interest has increased in photoresists that can be photoimaged with deep U.V. radiation. Such photoresists offer the potential of forming images of smaller features than may be possible at longer wavelength exposure. As is recognized by those in the art, "deep U.V. radiation" refers to exposure radiation having a wavelength in the range of about 350 nm or less, more typically in the range of about 300 nm or less. While a number of deep U.V. resists have been reported, the need clearly exists for new deep U.V. resists that can provide highly resolved fine line images as well as acceptable photospeed and other lithographic properties.

SUMMARY OF THE INVENTION

We have now discovered novel photoactive components that can exhibit excellent lithographic properties when used in either positive-acting or negative-acting photoresist compositions. Preferred photoactive components of the invention can be photoactivated upon exposure to deep U.V. radiation.

More particularly, in a first aspect, the invention provides a photoacid generator component that includes multiple aryl sulfonium compounds. Specifically, the photoactive component contains at least one multiple cation aryl sulfonium compound, preferably a di-cation compound. Preferred di-cation compounds include the aryl sulfonium salts of the following formula I:

wherein each R is the same or different and is a substituted or unsubstituted aryl group, and each M is a counter anion.

The photoactive component also preferably includes one or more single cation (mono-cation) aryl sulfonium PAGs (photoacid generators). Preferred mono-cation aryl sulfonium compounds include aryl sulfonium salts of the following formulae II and III:

wherein each R of formulae II and III is the same or different and is a substituted or unsubstituted aryl group, and each M is a counter anion.

Cyclic photoactive compounds also are suitable, including both mono-cation and multiple cation cyclic compounds. Preferred cyclic compounds may include one or more hetero atoms (particularly N, O or S) in addition to the sulfonium atom(s), or the sulfonium atom(s) may be the sole hetero atoms of the compound. For example, preferred cyclic photoactive compounds of the invention include those of the following formulae IV and V:

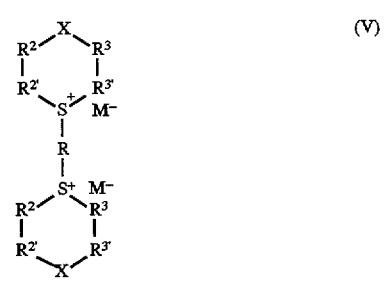

wherein each R is the same or different and is a substituted or unsubstituted aryl group; each $R^2$ and $R^{2'}$ are members of a first fused aryl ring; each $R^3$ and $R^{3'}$ are members of a second fused aryl ring; each X is independently a hetero atom, a $C_{1-3}$ alkylene, or a hetero-substituted $C_{1-3}$ alkylene; and each M is a counter anion.

Generally preferred compounds of formulae IV and V are those where $R^2$ and $R^{2'}$ are members of a first fused phenyl ring, and $R^3$ and $R^{3'}$ are members of a second fused phenyl ring, i.e. compounds of the following formulae where R, X and M are each the same as defined above for formulae IV and V:

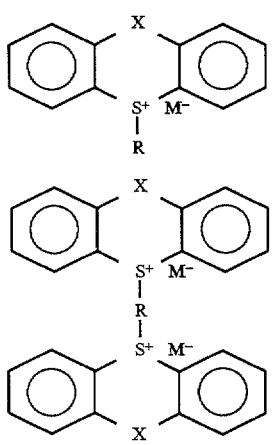

Upon exposure to activating radiation, including radiation having a wavelength in the deep U.V. range, compounds of the above formulae I through V generate an acidic photoreaction product that can provide a photoresist relief image.

Additionally, in a further aspect, the invention provides a photoactive component that includes a multiple cation sulfonium photoactive compound that is a carboxylate or sulfonate salt, preferably a sulfonate salt. The photoactive compound preferably is a di-cation compound, particularly compounds of the following formula VI:

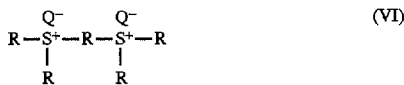

(VI)

wherein each R is the same or different and is a substituted or unsubstituted aryl group, and each Q is a sulfonate or carboxylate anion. These compounds may be used as the sole photoactive compound of a photoresist formulation.

It has been found that such photoactive compounds with organic sulfonate or carboxylate counter anions provide excellent lithographic properties when used as a photoresist photoactive component.

In particular, photoactive compounds of formula VI provide enhanced results relative to prior compounds that include non-organic counter anions such as a hexafluorophospate or an As-halide anion. For example, such prior compounds can pose solubility problems when formulated in an organic solvent-based resist composition. Additionally, use of such prior compounds in resist compositions can deposit metal (e.g. As) and P residues resulting in device contamination. In contrast, organic anions of compounds of formula VI impart good organic solvent solubility to the formula VI compounds. Also, it has been found that anions of formula VI are volatile at the elevated temperatures of standard post-exposure bake photoresist processing. The anions are thus removed prior to etching of a processed device surface and thereby avoid the contamination problems associated with the prior compounds.

The invention also provides photoresist compositions that comprise the above described photoactive components. Preferred photoresists of the invention include chemically-amplified resists, such as those negative-acting which undergo a photoacid-promoted crosslinking reaction to render exposed regions of a coating layer of the resist less developer soluble than unexposed regions, and those positive-acting resist compositions which undergo a photoacid-promoted deprotection reaction of acid labile groups of one or more composition components to render exposed regions of a coating layer of the resist more soluble in an aqueous developer than unexposed regions.

The invention also provide methods for forming relief images of the photoresists of the invention, including methods for forming highly resolved patterned photoresist images (e.g. a patterned line having essentially vertical sidewalls) of sub-micron and even sub-half micron dimensions.

In certain preferred aspects of the invention, the multiple aryl sulfonium compounds of a photoactive component can be conveniently prepared together without isolation of separate compounds, i.e. a "one-pot" synthesis.

The present invention further provides articles of manufacture comprising substrates such as a microelectronic wafer or a flat panel display substrate having coated thereon the photoresists and relief images of the invention. Other aspects of the invention are disclosed infra.

DETAILED DESCRIPTION OF THE INVENTION

Suitable aryl groups of the compounds of the photoactive component of the invention include aryl groups having 6 to about 18 or more carbons such as e.g. phenyl, naphthyl, anthryl, phenanthryl, pyrenyl, etc. Phenyl (substituted or unsubstituted) is a typically preferred aryl group.

Suitable M groups of compounds of the photoactive component include e.g. sulfonate groups such as alkyl sulfonates, particularly $C_{1-12}$ alkylsulfonates such as mesylate and the like; aryl tosylates, particularly $C_{6-18}$ aryl sulfonates such as tosylate; halogenated alkyl sulfonates, particularly halogenated $C_{1-12}$ alkylsulfonates such as triflate, and groups of the formula $CF_3(CF_2)_xSO_3$, where x is an integer of 1 to about 12 and the like; or a substituted or unsubstituted heteroaromatic or heteroalicyclic group having from 1 to 3 rings, typically one ring, 3 to 8 ring members in each ring and from 1 to 3 hetero (N, O or S) atoms. Carboxylates are also preferred M groups, e.g. groups of the formula $RCOO^-$ where R is substituted or unsubstituted alkyl having 1 to about 18 carbons or substituted or unsubstituted aryl such as phenyl or the like. Preferred substituents of such carboxy anions include e.g. halogen particularly fluoro. Those sulfonate and carboxylate groups are also suitable counter anions (Q groups) of compounds of formula VI above.

Additional preferred M groups of compounds of formulae I through V above include arsenic anions such as halogenated compounds, e.g. $AsF_6^-$; phosphonium compounds such as halogenated P compounds, e.g. $PF_6^-$; and borates such as alkyl and/or aryl substituted borate compounds, e.g. $B(C_6H_5)_4$.

Specifically preferred counter anions (M and Q of formulae I through VI) of photoactive compounds of the invention include, e.g., acetamidobenzenesulfonate;
2-acrylamido-2-methyl-1-propanesulfonate;
8-anilino-1-naphthyalenesulfonate;
benzylsulfonate;
t-butanesulfonate;
4-t-butylbenzenesulfonate;
camphorsulfonate;
di-(2-ethylhexyl)succinatesulfonate;
2,6-difluorobenzoate;
3,4-dimethoxybenzenesulfonate;
5-dimethylamino-1-naphthalenesulfonate;
3-(4-dimethylamino-1-naphthylazo)-4-methoxybenzenesulfonate;

4-[(4-dimethylamino)phenylazo]benzenesulfonate;
2,4-dinitrobenzenesulfonate;
(2-/3-/4-)-dodecylbenzenesulfonate;
ethanesulfonate;
4-fluorobenzenesulfonate;
hexadecanesulfonate;
hexafluorophosphate;
methanesulfonate;
(1-/2-)-naphthalenesulfonate;
4-octylbenzenesulfonate;
pentafluorobenzenesulfonate;
pentamethylbenzenesulfonate;
perfluorooctanesulfonate;
4-pyridineethanesulfonate;
3-pyridinesulfonate;
thymolblue;
4-toluenesulfonate;
2,4,5-trichlorobenzenesulfonate;
2,2,2-trifluoroethanesulfonate;
trifluoromethanesulfonate;
trifluoroacetate;
2-trifluoromethylbenzenesulfonate;
4-trifluoromethylbenzenesulfonate;
2,4,6-triisopropylbenzenesulfonate; and
2,4,6-trimethylbenzenesulfonate.

Preferred X groups of formulae IV and V include methylene ($CH_2$), S, O or N. Hetero-substituted $C_{1-3}$ alkylene include e.g. $C_{1-3}$ alkylene substituted by alkylthio having 1 to about 6 carbon atoms, alkoxy having 1 to about 6 carbon atoms or hydroxy.

Substituted R, $R^2$, $R^{2'}$, $R^3$, $R^{3'}$, M and Q groups are suitably substituted at one or more available positions by, e.g., halogen such as F, Cl Br and/or I, alkyl including $C_{1-16}$ alkyl with $C_{1-8}$ alkyl being preferred, alkoxy including $C_{1-6}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkenyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthryl and naphthyl, particularly phenyl. Substituted R and M groups also may be suitably substituted at one or more available positions by hetero atom containing groups, including groups containing one or more N, O and/or S atoms. Preferred groups include alkyl, alkenyl and alkynyl hetero-substituted groups, and hydroxyl, amino, and thio including alkylthio preferably having 1 to about 8 carbon atoms and one or more thio linkages as well as arylthio such as phenylthio.

Specifically preferred photoactive compounds of the invention include (thiodi-4,1-phenylene)bis (diphenylsulfonium) salt; a diphenyl-(4-phenylthio)phenyl sulfonium salt; a triphenylsulfonium salt; and a S-phenylthioanthrylium salt, i.e. the following compounds (A) through (D) shown as triflate salts:

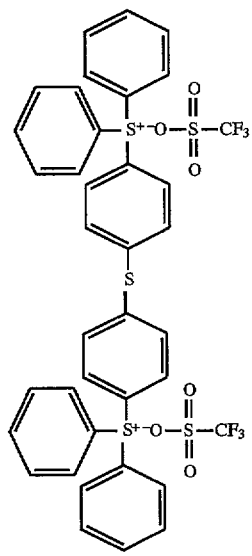

(A)

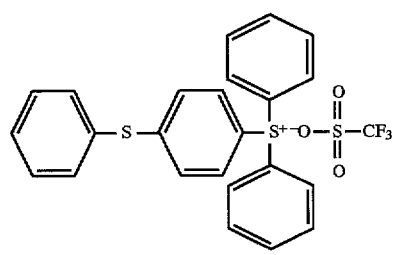

(B)

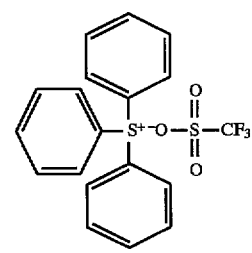

(C)

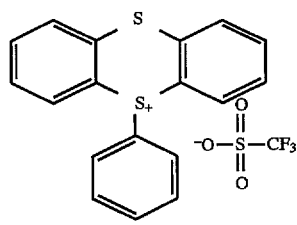

(D)

In certain embodiments, the photoactive component of the invention preferably comprises at least three distinct aryl sulfonium compounds, e.g. one multiple cation compound and two or more mono-cation aryl sulfonium compounds. The photoactive component also may suitably comprise more than one, e.g. two to about three or four, multiple cation aryl sulfonium compounds.

Compounds of the photoactive component of the invention can be readily prepared by methods known to those skilled in the synthesis art. For example, aryl compounds of formula III above can be prepared by reaction of an aryl Grignard reagent such as phenyl or naphthyl magnesium bromide or chloride and reacted with an aryl sulfoxide such as phenyl sulfoxide to provide the triarylsulfonium halide compound, e.g. where phenylmagnesiumbromide is reacted with phenyl sulfoxide, to provide triphenylsulfonium bromide. Other corresponding salts can be formed by known exchange reactions. See, for instance, Example 1(h) which follows.

Compounds of formula II can be prepared e.g. by reaction of a substituted or unsubstituted diaryl sulfoxide such as phenylsulfoxide with a substituted or unsubstituted arylsulfide such as phenyl sulfide under acidic conditions, followed by metathesis with the sulfonic acid of choice.

Compounds of Formula I can be prepared the acid-mediated condensation of an aryl sulfide, e.g. phenyl sulfide with two equivalents of a diaryl sulfoxide such as phenylsulfoxide. Subsequent metathesis of the intermediate onium salt with the sulfonic acid of choice affords the desired bis-sulfonate salt.

Compounds of Formula IV may be prepared by the copper (II) catalyzed arylation of an aryl sulfide in the presence of a diaryliodium salt. For example, reaction of thianthrene with diphenyliodonium triflate in the presence of a catalytic amount of copper (II) benzoate gives S-phenylthioanthrylium triflate in good yield. See also Example 1(k) which follows.

As discussed above, in certain preferred aspects of the invention, the multiple aryl sulfonium compounds of a photoactive component can be conveniently prepared together without isolation of separate compounds, i.e. a "one-pot" type of synthesis. In general, this synthetic approach provides condensation of one or more triarylsulfonium halide compounds in the presence of acid at room or elevated temperatures for a time sufficient to generate the desired mixture of aryl sulfonium compounds such as may be determined by conventional means e.g. chromatography or spectroscopy. See Example 1(a) which follows for such a one-pot synthesis.

As discussed above, the photoactive component of the invention are as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution. For example, preferred resin binders are phenolic resins including phenol aldehyde condensates known in the art as novolak resins, homo and copolymers of alkenyl phenols and homo and copolymers of N-hydroxyphenyl-maleimides.

Examples of suitable phenols for condensation with a aldehyde, especially formaldehyde, for the formation of novolak resins include phenol; m-cresol; o-cresol; p-cresol; 2,4-xylenol; 2,5-xylenol; 3,4-xylenol; 3,5-xylenol; thymol and mixtures thereof. An acid catalyzed condensation reaction results in formation of a suitable novolak resin which may vary in molecular weight from about 500 to 100,000 daltons. Poly(vinylphenols) may be prepared, e.g., as disclosed in U.S. Pat. No. 4,439,516. Preferred resin binders and the preparation thereof are also disclosed in U.S. Pat. No. 5,128,230.

Poly(vinylphenols) may be formed by block polymerization, emulsion polymerization or solution polymerization of the corresponding monomers in the presence of a catalyst. Vinylphenols useful for the production of polyvinyl phenol resins may be prepared, for example, by hydrolysis of commercially available coumarin or substituted coumarin, followed by decarboxylation of the resulting hydroxy cinnamic acids. Useful vinylphenols may also be prepared by dehydration of the corresponding hydroxy alkyl phenols or by decarboxylation of hydroxy cinnamic acids resulting from the reaction of substituted or nonsubstituted hydroxybenzaldehydes with malonic acid. Preferred polyvinylphenol resins prepared from such vinylphenols have a molecular weight range of from about 2,000 to about 60,000 daltons.

Copolymers containing phenol and nonaromatic cyclic alcohol units also are preferred resin binders for resists of the invention and may be suitably prepared by partial hydrogenation of a novolak or poly(vinylphenol) resin. Such copolymers and the use thereof in photoresist compositions are disclosed in U.S. Pat. No. 5,128,232 to Thackeray et al.

Further preferred resin binders include resins formed from bishydroxymethylated compounds, and block novolak resins. See U.S. Pat. Nos. 5,130,410 and 5,128,230 where such resins and use of same in photoresist compositions is disclosed. Additionally, two or more resin binders of similar or different compositions can be blended or combined together to give additive control of lithographic properties of a photoresist composition. For instance, blends of resins can be used to adjust photospeed and thermal properties and to control dissolution behavior of a resist in a developer.

A preferred class of photoresists of this invention are "conventional" positive-acting resists that comprise a photoactive component of the invention and a resin binder component such as a novolak or poly(vinylphenol) or partially hydrogenated derivative thereof and wherein the photoactive component serves as a dissolution rate inhibitor. Photoactivation of a coating layer of the resist results in conversion of the photoactive component to an acidic material, rendering regions of the coating layer containing this acidic photoproduct comparatively more soluble in an aqueous alkaline developer solution than regions that contain only the intact (non-activated) photoactive component.

In particularly preferred aspects of the invention, a photoactive component of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

A particularly preferred chemically amplified photoresist of the invention comprises in admixture a photoactive component of the invention and a resin binder that comprises a copolymer containing both phenolic and non-phenolic units. For example, one preferred group of such copolymers has acid labile groups substantially, essentially or completely only on non-phenolic units of the copolymer. One especially preferred copolymer binder has repeating units x and y of the following formula:

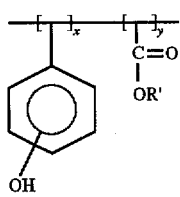

wherein the hydroxyl group be present at either the ortho, meta or para positions throughout the copolymer, and R' is substituted or unsubstituted alkyl having 1 to about 18 carbon atoms, more typically 1 to about 6 to 8 carbon atoms. Tert-butyl is a generally preferred R' group. An R' group may be optionally substituted by e.g. one or more halogen (particularly F, Cl or Br), $C_{1-8}$ alkoxy, $C_{2-8}$ alkenyl, etc. The units x and y may be regularly alternating in the copolymer, or may be randomly interspersed through the polymer. Such copolymers can be readily formed. For example, for resins of the above formula, vinyl phenols and a substituted or unsubstituted alkyl acrylate such as t-butylacrylate and the like may be condensed under free radical conditions as known in the art. The substituted ester moiety, i.e. R'—O—C(=O)—, moiety of the acrylate units serves as the acid labile groups of the resin and will undergo photoacid induced cleavage upon exposure of a coating layer of a photoresist containing the resin. Preferably the copolymer will have a $M_w$ of from about 8,000 to about 50,000, more preferably about 15,000 to about 30,000 with a molecular weight distribution of about 3 or less, more preferably a molecular weight distribution of about 2 or less. Non-phenolic resins, e.g. a copolymer of an alkyl acrylate such as t-butylacrylate or t-butylmethacrylate and a vinyl alicyclic such as a vinyl norbornanyl or vinyl cyclohexanol compound, also may be used as a resin binder in compositions of the invention. Such copolymers also may be prepared by such free radical polymerization or other known procedures and suitably will have a $M_w$ of from about 8,000 to about 50,000, and a molecular weight distribution of about 3 or less.

Another preferred resin binder for a positive chemically amplified resist of the invention has phenolic and nonaromatic cyclic alcohol units, wherein at least of portion of the hydroxyl groups of the copolymer are bonded to acid labile groups. Preferred acid labile moieties are acetate groups including t-butyl acetate groups of the formula $(CH_3)_3 COC(O)CH_2$—; oxycarbonyl groups such as t-butyl oxycarbonyl (t-Boc) groups of the formula $(CH_3)_3 CC(O)O$—; and acetal and ketals. Chemically amplified positive-acting photoresists containing such a copolymer have been disclosed in U.S. Pat. No. 5,258,257 to Sinta et al.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred additive of resist compositions of the invention is one or more sensitizer compounds that expand or enhance the resist's spectral response to activating radiation. Preferred photosensitizer compounds include aromatic compounds such as phenyl-based compounds, e.g. a substituted or unsubstituted benzene or a phenyl oligomer or polymer such as novolak or poly(vinylphenol) oligomer or polymer, naphthyl-based compounds as well as other fused ring compounds. More preferred are aromatic compounds that contain electron donating ring substituents such as hydroxy, alkoxy including alkoxy groups having from 1 to about 12 carbon atoms, preferably 1 to about 6 carbon atoms, alkyl including alkyl groups having from 1 to about 12 carbon atoms, preferably 1 to about 6 carbon atoms, and this groups including alkylthio groups having one or more this linkages and 1 to about 12 carbon atoms, preferably 1 to about 6 carbon atoms. Particularly preferred sensitizer compounds include phenyl or naphthyl substituted by one or more alkyl, hydroxy and/or alkoxy, particularly polyalkoxy phenyl and naphthyl, e.g. phenyl or naphthyl having from 2 to 6 alkoxy substituents, each alkoxy substituent having one or more oxygen linkages and from 1 to about 12 carbon atoms, more preferably 1 to about 6 carbon atoms. Specifically preferred sensitizer compounds include polyalkoxyphenyl compounds such as those compounds with alkoxy groups having from 1 to about 6 carbon atoms such as 1,2,3-trimethoxybenzene; polyhydroxyphenylalkyl compounds such as those compounds having a phenyl substituted alkyl group of 1 to about 6 carbon atoms such as trihydroxyphenyl ethane, particularly tris(4-hydroxyphenyl)ethane; bisphenol-A compounds; benzyl benzenetriol compounds such as a compound of the formula $C_6 H_5CH_2 C_6 H_2(OH)_3$; trihydroxybenzophenone; resorcinol; and pyrogallol. Such sensitizer compounds are suitably used in a resist composition of the invention in amounts of from 1 to about 30 percent by weight of the total weight of a resist's dry components, more preferably in amounts of from 5 to about 20 weight percent.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists. It is also generally preferred that the multiple cation aryl compound(s) comprise from about 30 to 80 weight percent of the photoactive component, with one or more of the mono-cation compounds comprising the remainder of the photoactive component. Preferred photoactive components include those that contain about 50 to 70 weight percent of a di-cation photoactive compound such as the triflate compound (A) shown above; about 5 to 10 weight percent of mono-cation compound such as the triflate compound (B) shown above; and about 0.5 to 10 weight percent of other mono-cation compounds such as a mixture of the triflate compounds (C) and (D) shown above.

The photoresists of the invention are generally prepared following known procedures with the exception that a photoactive component of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methhoxyethyl ether (diglyme), ethylene glycol monomethyl ether, propylene glycol monomethyl ether; lactates such as ethyl lactate or methyl lactate, with ethyl lactate being preferred; proponiates, particularly methyl propionate and ethyl propionate; a Cellosolve ester such as methyl Cellosolve acetate; an aromatic hydrocarbon such toluene or xylene; or a ketone such as methylethyl ketone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 10 to 300 mJ/cm$^2$. An exposure wavelength in the deep U.V. range often preferably will be used for the photoresists of the invention, particularly an exposure wavelength of about 248 nm. Suitable post-exposure bake temperatures are from about 50° C. or greater, more specifically from about 50 ° to 140° C. For an acid-hardening negative-acting resist, a post-development bake may be employed if desired at temperatures of from about 100 ° to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

All documents mentioned herein are incorporated herein by reference.

The following non-limiting examples are illustrative of the invention.

EXAMPLE 1

Preparation of photoactive compounds of the invention

Example 1(a)

Preparation of admixture of triphenylsulfonium triflate photoacid generators

A 2 L reaction flask was charged with 600 ml water and 45.1 g (0.300 mol) triflic acid, added slowly by addition funnel with stirring. 200.0 g (0.300 mol, based on a mol. wt. of 333 ) of triarylsulfonium chloride (50% aqueous solution) was added and washed in with 100 ml water followed by 700 ml of methylene chloride. The reaction mixture was stirred vigorously for 18 hours at 25° C. The organic phase was separated and washed with water (3×300 ml) until pH=7. The methylene chloride was removed by evaporation until a viscous foaming oil remained. The product, a mixture of compounds (A) through (D) above, was dried under vacuum at 70° C. for 24 hours leaving a tan solid (110 g, 82%); m.p. 53°–82° C.; $\epsilon248=11,739$ (based on an estimated mol. wt.=447 ); Ta=393° C. (TGA, 5% weight loss, 10° C./min.).

Example 1(b)

Preparation of Triphenylsulfonium 5-dimethylamino-1-naphthalenesulfonate (TASDANS) (via base containing sulfonic acid in the presence of ammonium hydroxide)

To a suspension of 5-dimethylamino-1-naphthalenesulfonic acid (12.57 g, 50.0 mmol) in water (90 ml) at room temperature was added concentrated ammonium hydroxide (29.8%, 14.5 M, 3.45 ml, 50.0 mmol). The brownish suspension turned dark green and the majority of the acid dissolved. Triphenylsulfonium chloride (50% aqueous solution, 29.80 g) was added over 15 minutes. After stirring the two phase system for 30 minutes, dichloromethane (100 ml) was added and the mixture stirred at room temperature for 14 hours. Additional dichloromethane (300 ml) was added and the layers separated. The organic layer was washed with water (6×150 ml) until the washings were neutral (pH 7 ). After drying (MgSO$_4$ ), the solvent was removed in vacuo to give the onium salt as a pale yellow foam. The product was rigorously dried by heating at 90°–100° C. for 60 hours under vacuum. In this way, triphenylsulfonium 5 -dimethylamino-1-naphthalenesulfonate was isolated as a pale yellow foam (23.35 g).

IR (KBr) υ 1209, 1201, 1192, 1085, 1015, 677 cm$^{-1}$. $^1$H NMR δ (CDCl$_3$ ) 2.73 (6H, s, 5-N(CH$_3$ )$_2$ ), 6.95 (1H, d, DANS-H), 7.00–7.95 (complex m, 2H from DANS moiety plus Ar$_3^+$), 8.06 (1H, d, DANS-H), 8.15 (1H, d, DANS-H), 8.67 (1H, d, DANS-H) ppm. UV(MeCN) ε (λ max) 13659 (304 nm), [$\epsilon_{254}$=17038, $\epsilon_{248}$=21879].

Example 1(c)

Preparation of Triphenylsulfonium perfluorooctanesulfonate (via sulfonate salt)

To a suspension of perfluorooctanesulfonic acid potassium salt (24.64 g, 46.1 mmol) in water (150 ml) at room temperature under nitrogen was added dropwise triphenylsulfonium chloride (50% aqueous solution, 27.50 g) over 15 minutes. After stirring the suspension for 30 minutes, dichloromethane (75 ml) was added and the mixture stirred at room temperature for 20 hours. Additional dichloromethane (225 ml) was added and the layers separated. The organic layer was washed with water (5×125 ml) until the washings were neutral (pH 7). After drying (MgSO$_4$), removal of the solvent in vacuo gave a viscous gum which was further dried by heating at 80°–90° C. for 84 hours under vacuum. In this way, triphenylsulfonium perfluorooctanesulfonate was isolated as a glassy solid (30.61 g).

IR (KBr) υ 1263, 1210, 1150, 1122, 745 cm$^{-1}$. $^1$H NMR δ (CDCl$_3$) 7.25–7.90 (complex m, Ar$_3$ S$^+$) ppm. UV(MeCN) ε (λ max) 11206 (269 nm, sh), 12543 (279 nm, sh), 13693 (295 nm), [ε$_{254}$=11346, ε$_{248}$=15030].

Example 1(d)

Preparation of Triphenylsulfonium 4-trifluoromethyl benzenesulfonate (via sulfonyl hydrolysis)

A suspension of 4-trifluoromethylbenzenesulfonyl chloride (20.53 g, 83.9 mmol) in water (150 ml) containing sodium carbonate (9.43 g, 88.10 mmol) was heated at reflux for 22 hours. After cooling to room temperature, triphenylsulfonium chloride (50% aqueous solution, 50.00 g) was added over 15 minutes. After stirring the biphasic mixture for 30 minutes, dichloromethane (300 ml) was added and the mixture stirred at room temperature for 20 hours. The layers were separated and the organic layer washed with water (7×150 ml) until the washings were neutral (pH 7). After drying (MgSO$_4$), removal of the solvent in vacuo gave a pale yellow foam which was further dried by heating at 80°–100° C. for 108 hours under vacuum. In this way, triphenylsulfonium 4-trifluoromethylbenzenesulfonate was isolated as a pale yellow glass (36.77 g).

IR (KBr) υ 1324, 1210, 1166, 1122, 1066, 1009, 715 cm$^{-1}$; $^1$H NMR δ (CDCl$_3$) 7.17–7.88 (complex m, Ar$_3$ S$^+$), 7.53 and 7.91 (each 2H, AB$_q$) ppm. UV(MeCN) ε (λ max) 9334 (278 nm sh), 10200 (294 nm), [ε$_{254}$=8668, ε$_{248}$=11274].

Example 1(e)

Preparation of triphenylsulfonium bromide

To a 3-necked 1 L round bottom flask equipped with a still head was added phenylmagnesium bromide (3 M in diethyl ether, 142 ml, 0.426 mol) followed by dry benzene (150 ml). The flask was connected to a water aspirator and the diethyl ether removed under vacuo by gently heating. Additional benzene (150 ml) was added and the solution brought to a gentle reflux under nitrogen. A solution of phenyl sulfoxide (17.23 g, 85.2 mmol) in benzene (100 ml) was added dropwise over 1.5 hours. Once the addition was complete, the reaction mixture was heated at a gentle reflux for 3 hours. The reaction mixture was cooled (ice bath temperature) while adding a solution of hydrobromic acid (25%, 200 ml). The resulting biphasic mixture was stirred at room temperature overnight. After separation of the layers, the organic layer extracted were combined and extracted with dichloromethane (200 ml), dried (MgSO$_4$) and concentrated in vacuo to give the crude product as an off-white solid (14.50 g). The solid was taken up in the minimum mount of warm dichloromethane (100 ml) and four times the volume of ether added to precipitate the salt. The suspension was cooled in an ice bath for 1 hour prior to collecting the salt and washing with ether. In this way, triphenylsulfonium bromide was isolated as a white solid (14.40 g, 49%).

m.p. 293°–294° C. (lit. 285°–287° C.). Microanalysis: Calculated for C$_{18}$H$_{15}$BrS (343.27); C 62.98, H 4.40, Br 23.38, S 9.34; Found C 62.72, H 443, Br 23.35, S 9.62%. $^1$H NMR (CDCl$_3$) δ 6.60–7.82 (9H, m, 3×3,4,5-H), 7.83–7.93 (6H, m, 3×2,6-H) ppm. $^{13}$C NMR (CDCl$_3$) δ 124.22, 131.00, 131.31, 134.30 ppm.

Example 1(f)

Preparation of Triphenylsulfonium Tosylate

A solution of triphenylsulfonium bromide (6.87 g, 20.0 mmol) and p-toluenesulfonic acid (3.80 g, 20.0 mmol) in water (100 ml) was heated at a gentle reflux for 15 hours under nitrogen. After cooling to room temperature, the clear solution was extracted with dichloromethane (4×75 ml). The combined organic extracts were washed with water until neutral (4×75 ml) and dried (MgSO$_4$). The solvent was removed under reduced pressure and the residue dried by heating at 80° C. in vacuo for 36 hours to give a crude onium salt as a off-white solid (6.35 g). Recrystallization from acetone-ethyl acetate gave triphenylsulfonium rosylate as a white crystalline solid (5.72 g, 66%).

m.p. 116°–118° C. TGA: T$_d$ (5% wt. loss)=316° C. Microanalysis: Calculated for C$_{25}$ H$_{22}$O$_3$ S$_2$ (434.55); C 69.09, H 5.10, S 14.76; Found C 68.33, H 5.08, S 14.63%. $^1$H NMR (CDCl$_3$) δ 2.29 (3H, s, 4-CH$_3$), 7.06 (2H, d (J=8.1 Hz), Ts 3,5-H), 7.58–7.84 (17H, m, Ts 2,6-H+Ar$_3$ S$^+$) ppm. $^{13}$C NMR (CDCl$_3$) δ 21.27 (4-CH$_3$), 124.80 (Ph, 4-C), 126.15 (Ts, 2-C), 128.28 (Ts, 3-C), 131.34 (Ph 3-C), 131.42 (Ph, 2-C), 134.33 (Ph, 1-C), 138.42 (Ts, 4-C), 144.78 (Ts, 1-C) ppm. HPLC analysis indicated the TPSOTs had a purity of 99.7%.

Example 1(g)

Preparation of Diphenyl 4-thiophenoxyphenylsulfonium Tosylate

To a mixture of diphenylsulfoxide (20.23 g, 0.10 mol) and diphenylsulfide (18.63 g, 0.10 mol) at −5° C. (ice/acetone cooling bath) was added phosphorous pentoxide-methane sulfonic acid reagent (1:10 by wt, 40 ml) in one portion with vigorous stirring. A slight isotherm was observed at the temperature rose to 10° C. and the returned to 0° C. soon after. The resulting orange brown suspension was stirred at 0° C. for 1 hour and then warmed up to room temperature and stirred thereat for 2 hours. During this time, the reaction mixture formed a deep purple solution. This solution was diluted with water (200 ml) and the resulting cloudy solution treated with a solution of p-toluenesulfonic acid (19.02 g, 0.10 mol) in water (100 ml). The resulting milky suspension was stirred at room temperature for 15 hours, dichloromethane (250 ml) was added and the layers separated. The aqueous layer was extracted with additional dichloromethane (3×100 ml). The organic extracts were combined and washed with water (3×250 ml) until the washings were neutral. After drying (MgSO$_4$), removal of the solvent in vacuo gave a orange gum which was further dried by heating at 90°–100° C. in vacuo for 72 hours. After drying, the material formed an orange glass (45.78 g). Analysis by $^{13}$C NMR spectroscopy and TLC (EtOAc) indicated the crude product was contaminated by traces of the starting sulfide (d 135.30 for quaternary C, R$_f$ 0.86) and sulfoxide (d 145.13 for quaternary C), R$_f$ 0.73) respectively. A portion of this material (15.4 g) was purified by dry flash chromatography using a sintered glass funnel of silica gel. Initial elution with dichloromethane allowed removal of the less polar impurities along with some mixed fractions. Increasing the eluant polarity to 5% MeOH/95% dichloromethane allowed isolation of the desired onium salt as an orange foam. After drying by heating at 70°–80° C. in vacuo for 48 hours, the title compound isolated as a hygroscopic orange glass (6.80 g, 37% based on aliquot taken).

TGA: $T_d$ (5% wt loss)=320° C. Microanalysis: Calculated for $C_{31}H_{26}O_3S_3$ (542.71); C 68.60, H 4.83, S 17.72; Found C 68.04, H 5.10, S 17.39%. $^1$H NMR (CDCl$_3$) δ 2.28 (3H, s, 4-CH$_3$), 7.04 (2H, d), 7.20 (2H, 7.40–7.85 (19H, m) ppm. $^{13}$C NMR (CDCl$_3$) δ 20.91 (4-CH3), 119.44 (Ar, 5-C), 124.63 (At, 4-C), 125.74 (Ts, 2-C), 127.85, 127.89 (Ts, 3-C), 128.91, 129.63, 129.80, 130.65, 131.02, 131.41, 133.88, 134.65, 138.03 (Ts, 4-C), 144.44 (Ts, 1-C), 148.45 (At, 8-C) ppm. UV HPLC analysis indicated the DTSOTs had a purity of 99.4%.

Example 1(h)

Preparation of Bis [4-(diphenylsulfonio)phenyl]sulfide-bis-tosylate via Bis [4-(diphenylsulfonio)phenyl]sulfide-bis-iodide To a warm solution of his [4-(diphenylsulfonio)phenyl] sulfide-bis-iodide (7.79 g, 10.0 mmol, 75.5% BDSI) in methanol 100 ml) was added p-toluenesulfonic acid silver salt (5.86 g, 21.0 mmol) in one portion. The suspension was stirred at a gentle reflux for 14 hours. After cooling, the silver iodide precipitate was filtered off and washed with methanol (3×50 ml). The filtrate was concentrated under reduced pressure and the residue dried in vacuo at 120° C. for 24 hours to give the crude product as a light brown glass (9.45 g). TLC analysis (10% MeOH-90% CH$_2$Cl$_2$) indicated the crude product was a complex mixture. HPLC indicated the crude product contained the title compound BDS cation in a purity of 89.8%.

Example 1(i)

Preparation of Bis [4-(diphenylsulfonio)phenyl]sulfide-bis-triflate (BDSOTf)

Preparation of 4,4'-Dibromophenylsulfide

To a well stirred solution of phenyl sulfide (93.14 g, 0.50 mol) in glacial acetic acid (500 ml) at 15°–20° C. was added dropwise bromine (167.81 g, 1.05 mol) over 1.5 hours. Towards the end of the addition, the temperature rose to 30°–35° C. and a yellow precipitate formed. Once the addition was over, the reaction mixture was warmed to 55°–65° C. and stirred therat for 2.5 hours. During this time a substantial amount of solid precipitated from solution. After cooling, the solid was collected by suction filtration, and washed with water (1 L). The filter cake was reslurried in water (1.5 L) for 45 minutes and the collected by suction filtration and washed with water (1 L). The filter cake was dried under aspirator vacuum for 1 hour and then dried in vacuo at 60° C. for 14 hours. The crude product was recrystallized from dichloromthane-hexane to give 4,4'-dibromophenylsulfide as a white solid (109.10 g). Additional 4,4'-dibromophenylsulfide (21.69 g) was isolated from the mother liquor by repeated recrystallization from chloroform-ethanol (1:1) and ethanol. Total yield of 4,4'-dibromophenylsulfide amounted to 130.79 g, 76%.

m.p. 113°–114° C. Microanalysis: Calculated for $C_{24}H_8Br_2S$ (344.07); C 41.89, H 2.34, S 9.32; Found C 42.05, H 2.54, S 9.42%. $^1$H NMR δ (CDCl$_3$) 7.17 and 7.42 (each 4H, AB$_q$ ($J_m$=8.5 Hz, $J_m$=2.5 Hz), 2.2',6,6'-H and 3,3',5,5'-H) ppm.

Preparation of 1,1'-Thiobis[4-(phenylthio)benzene]

A mixture of 4,4'-dibromophenylsulfide (15.01 g, 44.0 mmol), thiophenyl (10.58 g, 96.0 mmol) and potassium carbonate (13.30 g, 96.0 mmol) in dimethylformamide (100 ml) was heated at reflux under nitrogen for 20 hours with vigorous mechanical stirring. After cooling, the mixture was poured into water (300 ml) and the solid extracted with dichloromethane (3×200 ml). The combined organic extracts were washed with water (3×200 ml) and brine (1×100 ml) and dried (MgSO$_4$). Removal of the solvent in vacuo gave a white solid which was purified by recrystallization from chloroform-ethanol. In this way, 1, 1'-thiobis [4-(phenylthio)benzene] was isolated as a white solid (16.50 g, 93%).

m.p. 109°–110° C. Microanalysis: Calculated for $C_{24}H_{18}S_3$ (402.57); C 71.60, H 4.51, S 23.89; Found C 70.94, H 4.70, S 23.68%. $^1$H NMR δ (CDCl$_3$) 7.14–7.39 (18H, complex m, all ArH) ppm. $^{13}$C NMR δ (CDCl$_3$) 127.42, 129.23, 130.85, 131.45, 131.58, 133.86, 134.61, 135.49 ppm.

Preparation of Bis[4-(diphenylsulfonio)phenyl]sulfide-bis-triflate (BDSOTf)

a) Via copper (II) catalyzed route,

A 50 ml round bottom flask was charged with 1,1'-thiobis[4-(phenylthio)benzene] 4.03 g, 10.0 mmol), diphenyliodonium triflate (8.50 g, 20.0 mmol) and a catalytic amount of copper (II) benzoate (0.183 g). The flask was fitted with a condenser and heated under nitrogen in an oil bath at 150° C. for 14 hours. At this point, TLC analysis (10% MeOH-90% CH$_2$Cl$_2$) indicated the product was complex mixture of onium components. The red oily product was taken up in dichloromethane and loaded onto a dry flash chromatography column (125 g flash SiO$_2$ in a sintered glass funnel [75 mm tall×85 mm id]). Gradient elution with CH$_2$Cl$_2$, 1% MeOH-99% CH$_2$Cl$_2$, and finally 2.5% MeOH-97.5% CH$_2$Cl$_2$ was performed until the major components were eluted. After drying, the two major components were isolated as pale yellow orange glassy solids; 2.11 g and 1.09 g respectfully. Although seemingly pure by TLC, HPLC analysis indicated these two fractions were substantially impure. Other mixed fractions were isolated as a waxy solid (2.54 g) from the column. Trituration of these latter mixed fractions with dichloromethane gave a pale yellow solid which amounted to 1.90 g from two crystal crops. By TLC, the purity of this material was greatly improved over the crude reaction mixture. Small test samples of this solid were readily recrystallized from iso-propanol or dichloromethanebutyl acetate. Based on this, the bulk of this material (1.80 g) was further purified by recrystallization. Crystallization occurred rapidly upon addition of butyl acetate (10 ml) to a solution of the solid in hot dichloromethane (40 ml). The suspension was cooled to room temperature and stored in a refrigerator for 64 hours. The crystals were filtered off, washed with butyl acetate (2×10 ml) and hexane (1×20 ml) and dried in vacuo at 60°–70° C. for 24 hours to give a white solid (1.63 g). Both $^1$H NMR and TGA analysis indicated this material contained a substantial amount of residual solvent (@7 wt %). The solid was dired further by heating at 120° C. for 24 hours in vacuo to give the product as a white crystalline solid (1.48 g, 17%). TLC (10% MEOH-90% CH$_2$Cl$_2$) indicated this material was chromatographically homogeneous. Based on the following analytical data, this material was identified as BDSOTf.

M.P. 170.5°–171.5° C. TGA: $T_d$ (5% wt loss)=406° C. Microanalysis: Calculated for $C_{38}H_{28}F_6O_6S_5$ (854.92); C 53.38, H 3.30, F 13.33, S 18.75; Found C 53.32, H 3.55, F 13.69, S 18.72%. $^1$H NMR δ (Me$_2$CO-d$_6$) 7.80–7.89 (12H, complex m), 7.90–8.00 (16H, complex m) ppm. $^{13}$C NMR δ (Me$_2$CO-d$_6$) 121.41 (q, CF$_3$, JCF=321.6 Hz), 123.98, 124.94, 131.41, 131.60, 132.47, 132.94, 134.71, 142.00 ppm. HPLC analysis indicated the BDSOTf had a purity of 93%.

b) Using phosphorous pentoxide-methanesulfonic acid dehydrating reagent

To a mixture of diphenylsulfoxide (40.46 g, 0.20 mol) and diphenylsulfide (18.63 g, 0.10 mol) at room temperature under nitrogen was added phosphorous pentoxide-methane sulfonic acid reagent (1:10 by wt, 80 ml) in two portions with vigorous stirring. A slight exotherm was observed during addition and the resulting pale green homogeneous solution was stirred at room temperature for 18 hours. This solution was diluted with water (250 ml) and the resulting clear solution treated with neat triflic acid (30.02 g, 0.20 mol). The resulting milky suspension was stirred at room temperature for 3 hours, then dichloromethane (200 ml) was added and biphasic mixture stirred for 2 hours. The layers were separated and the aqueous layer extracted with additional dichloromethane (2×150 ml) until the washings were neutral. After drying ($MgSO_4$), removal of the solvent in vacuo gave a orange gum which was further dried by heating at 100° C. in vacuo for 48 hours. During drying the material formed a pale orange glass (79.13 g). TLC analysis (10% MeOH-90% $CH_2 Cl_2$) indicated the crude product was a complex mixture in which BDSOTf was present. HPLC indicated the crude product contained BDSOTf in 28.2%.

A portion of this mixture (77.86 g) was taken up in hot dichloromethane (300 ml), filtered and allowed to cool to room temperature. Butyl acetate (100 ml) was added to give a slightly turbid solution. The solution was cooled in an ice bath until crystallization started and then allowed to stand at room temperature for 15 hours. The solid was collected, washed with dichloromethane-butyl acetate (1:1, 2×25 ml) and dried in vacuo at 120° C. for 24 hours. During drying, the solid partially melted giving off-white glassy plates (8.26 g). Trituration of the mother liquor gave two more crystal crops which amounted to 5.44 g and 5.82 g after drying as above. The crystal crops were combined and recrystallized from $CH_2 Cl_2$-BuAc. The resulting crystals were washed with $CH_2 Cl_2$-BuAc (1:3, 2×25 ml) and ether (1×50 ml) and dried in vacuo at 60° C. for 12 hours followed by 120° C. for 36 hours. In this way BDSTf was isolated as off-white cream platelets (17.22 g, 20%). HPLC analysis indicated the BDSOTf had a purity of 97.6%.

c) Using sulfuric acid as dehydrating reagent at room temperature

To a well stirred solution of diphenylsulfoxide (21.24 g, 0.105 mol) in concentrated sulfuric acid (100 ml) at room temperature under nitrogen was added diphenylsulfide (9.31 g, 0.05 mol) dropwise over 2.5 minutes. The reaction mixture changed color and a slight exotherm was observed. The mixture was stirred for 1.5 hours and then poured into a solution of triflic acid (15.01 g, 0.10 mol) in water (150 ml). The reaction mixture became very hot and on cooling a yellow oil separated from the aqueous solution. The mixture was stirred at room temperature for 2 hours, dichloromethane (200 ml) was added and the biphasic mixture was stirred for 62 hours. The layers were separated and the aqueous layer extracted with additional dichloromethane (3×100 ml). The combined organic extracts were washed with water (5×200 ml) until the washings were neutral. After drying ($MgSO_4$), removal of the solvent in vacuo gave a white foam which was further dried by heating at 100° C. in vacuo for 48 hours. During drying, the material formed in pale yellow glass (36.26 g). TLC analysis (10% MeOH-90% $CH_2 Cl_2$) indicated the crude product contained BDSOTf in 70.1%.

A portion of this mixture (35.26 g) was taken up in hot dichloromethane (200 ml), filtered and allowed to cool to room temperature. Butyl acetate (75 ml) was added to give a slightly turbid solution the solution was cooled in an ice bath until crystallization started and then allowed to stand at room temperature for 15 hours. The solid was collected, washed with dichloromethane-butyl acetate (1:2, 2×25 ml) and ether (1×50 ml) and dried in vacuo at 120° C. for 62 hours. During drying, the solid partially melted giving off-white glassy plates (8.26 g). The solid was recrystallized again from $CH_2 Cl_2$-BuAc. The resulting crystals were washed with $CH_2 Cl_2$-BuAc (1:3, 2×25 ml) and ether (1×50 ml) and dried in vacuo at 60° C. for 12 hours followed by 120° C. for 62 hours. During drying, the solid partially melted diving off-white glassy plates (8.26 g). The solid was recrystallized again from $CH_2 Cl_2$-BuAc. The resulting crystals were washed with $CH_2 Cl_2$-BuAc (1:3, 2×25 ml) and ether (1×50 ml) and dried in vacuo at 60° C. for 12 hours followed by 120° C. for 36 hours. In this way BDSOTf was isolated as off-white cream platelets (12.78 g, 30%). HPLC analysis indicated the BDSOTf had a purity of 91.3%.

d) Using sulfuric acid as dehydrating reagent with cooling

To a well stirred solution of diphenylsulfoxide (21.24 g, 0.105 mol) in concentrated sulfuric acid (100 ml) at −5°–0° C. under nitrogen was added diphenylsulfide (9.31 g, 0.05 mol) in one portion. No exotherm was observed in the reaction mixture was allowed to stir at 0° C. for 15 minutes then allowed to warm up to room temperature with stirring over 1.5 hours. The reaction mixture was poured into water (200 ml) with ice bath cooling and the resulting solution treated with neat triflic acid (15.01 g, 0.10 mol). The cloudy mixture was stirred at room temperature for 45 mutes, dichloromethane (100 ml) was added and the biphasic mixture stirred for 15 hours. The mixture was diluted with water (200 ml) and dichloromethane (100 ml). The layers were separated and the aqueous layer extracted with additional dichloromethane (3×150 ml). The combined organic extracts were washed with water (5×200 ml) until the washings were neutral. After drying ($MgSO_4$), removal of the solvent in vacuo gave a white foam which was further dried by heating at 100° C. in vacuo for 48 hours. During drying, the material formed a pale yellow glass (39.10 g). TLC analysis (10% MeOH-90% $CH_2 C12$) indicated the crude product was a complex mixture in which BDSOTf was present. HPLC indicated the crude product contained BDSOTf in 83.6%.

A portion of this mixture (37.91 g) was recrystallized from dichloromethane (100 ml)-butyl acetate (50 ml) by allowing to stand at room temperature for 2 hours. The solid was collected, washed with dichloromethane-butyl acetate (1:4, 2×40 ml) and dried in vacuo at 120° C. for 36 hours. During drying, the solid partially melted giving large creamy white platelets (29.96 g). The solid was recrystallized again from $CH_2 Cl_2$ (75 ml)-BuAc (35 ml). The resulting crystals were washed with $CH_2 C12$-BuAc (1:4, 2×50 ml) and dried in vacuo at 120° C. for 36 hours. In this way, BDSOTf was isolated as large creamy white platelets (25.91 g, 61%). HPLC analysis indicated the BDSOTf had a purity of 96.0%.

EXAMPLE 2

Preparation and imaging of a photoresist of the invention

Five different photoresists (identified as resists A through E below and in the Table) by admixing 1) a resin binder that was 14% t-butylacetate blocked polyvinyl phenol (2% hydrogenated), 2) a photoacid component (at 5% loading based on resin binder weight) and 3) ethyl lactate (casting solvent).

The resin binder was prepared by reaction of a 2% hydrogenated poly(vinyl)phenol (Maruzen Oil, Tokyo Japan; % hydrogenation indicates the mole % of nonaromatic cyclic alcohol units of the resin) with t-butylchloroacetate. The percent substitution of the hydroxyl groups of the PVP resin by t-butyl acetate groups was confirmed by NMR.

Each of the resists A through E had a different photoactive component. The photoactive component of resist A was the mixture of compounds produced through the method of Example 1 above. The photoactive component of resist B consisted of a single compound of triphenylsulfonium triflate (compound C above). The photoactive component of resist C consisted of a single compound of diphenyl-[4-phenylthio)phenyl]sulfonium triflate (compound B above). The photoactive component of resist D consisted of a single compound of (thio-4,1-phenylene)bis (diphenylsulfonium) ditriflate) (compound A above). The photoactive component of resist F, also consisted of a single compound of S-phenylthioanthrylium triflate (compound D above).

The resist formulations were each spin coated onto separate HMDS oven vapor primed 4" silicon wafers to a thickness of 7200±25 angstroms. The film thickness was measured using a Prometric SM300. All of the spin coated wafers were soft baked at 110° C. for 60 seconds. The wafers were exposed on a GCA ALS, DUV excimer laser stepper (KrF laser, NA=0.35, wavelength=248 nm) and post baked at 88° C. for 120 seconds. The resist was developed using a 20/25 second double spray puddle development program with a 0.21N aqueous tetramethylammonium hydroxide solution.

The Table below shows the photospeed ($E_o$), which was calculated as the exposure dose necessary to remove the indicated resist film upon development. The energy to size ($E_s$), unexposed film thickness loss (UFTL), the resolution, and the resist profiles were also determined.

TABLE

| Resist # | $E_o$ (mJ/cm$^{-2}$) | $E_s$ (mJ/cm$^{-2}$) | $E_s/E_o$ | Resolution (μm) Comment | % UFTL |
|---|---|---|---|---|---|
| A | 18.6 | 47.8 | 2.57 | 0.32 Slightly Rounded | 3.31 |
| B | 12.0 | 18.8 | 1.57 | 0.40 Rounded Profiles | 28.7 |
| C | 21.5 | 51.1 | 2.38 | 0.32 Square Profiles | 2.6 |
| D | 16.5 | 37.2 | 2.25 | 0.32 Square Profiles | 3.5 |
| E | 30.6 | 51.1 | 1.67 | 0.38 Slightly Rounded | 15.5 |

The foregoing description of the invention is merely illustrative thereof, and it is understood that variations and modifications can be effected without departing from the spirit or scope of the invention as set forth in the following claims.

What is claimed is:

1. A photoresist composition comprising:
 a resin binder and a photoactive component in an mount sufficient to permit development of an exposed coating layer of the composition,
 the photoactive component comprising a plurality of distinct aryl sulfonium photoactivatable compounds including at least one aryl sulfonium compound of the following formula (I):

wherein each R is the same or different and is a substituted or unsubstituted aryl group, and each M is a counter anion.

2. The photoresist composition of claim 1 wherein each R is independently a substituted or unsubstituted phenyl.

3. The photoresist composition of claim 1 wherein the photoactive component comprises at least one aryl sulfonium compound having a single cation.

4. The photoresist composition of claim 3 wherein the photoactive component comprises one or more compounds selected from the following formulae II or III:

wherein each R of said formulae is the same or different and is a substituted or unsubstituted aryl group, and each M of said formulae is a counter anion.

5. The photoresist composition of claim 4 wherein each R is a substituted or unsubstituted phenyl.

6. The photoresist composition of claim 4 wherein one or more M groups is triflate.

7. The photoresist composition of claim 1 wherein the photoactive component comprises one or more cyclic aryl sulfonium compounds.

8. The photoresist composition of claim 7 wherein the photoactive component comprises one or more compounds of the following formulae (IV) and (V):

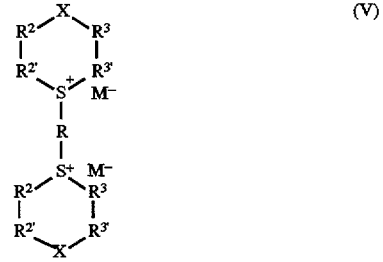

wherein each R is the same or different and is a substituted or unsubstituted aryl group; each $R^2$ and $R^{2'}$ are members of a first fused aryl ring; each $R^3$ and $R^{3'}$ are members of a second fused aryl ring; each X is independently a hetero atom, a $C_{1-3}$ alkylene, or a hetero-substituted $C_{1-3}$ alkylene; and each $M^-$ is a counter anion.

9. The photoresist composition of claim 8 wherein the photoactive component comprises one or more of a (thiodi-4,1-phenylene)bis(diphenylsulfonium) salt, a diphenyl-(4- phenylthio)phenyl sulfonium salt, a triphenylsulfonium salt and a S-phenylthioanthrylium salt.

10. The photoresist of claim 1 wherein substituted R groups are substituted at one or more available positions by halogen; $C_{1-16}$ alkyl; $C_{1-16}$ alkoxy; $C_{2-12}$ alkenyl; $C_{2-12}$ alkynyl; aryl; aryl substituted by halo, alkoxy, alkenyl, alkynyl or alkyl; heteroalkyl; heteroalkenyl; heteroalkynyl; hydroxyl; amino; alkylthio; and arylthio.

11. The photoresist composition of claim 1 wherein the composition is a chemically amplified positive-acting photoresist.

12. The photoresist composition of claim 1 wherein the composition is a negative-acting photoresist.

13. An article of manufacture having on at least one surface a coating layer of the photoresist composition of claim 1.

14. A method for forming a photoresist relief image on a substrate comprising:
(a) applying a coating layer of a photoresist composition of claim 1 on a substrate; and
(b) exposing the photoresist coating layer to patterned activating radiation and developing the exposed photoresist layer to provide a relief image.

15. The method of claim 14 wherein the plurality of aryl sulfonium compounds are formed together in a one-pot reaction.

16. A photoresist composition comprising:
a resin binder and a photoactive component in an amount sufficient to permit development of an exposed coating layer of the composition,
the photoactive component comprising a compound of the following formula VI:

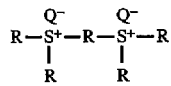

(VI)

wherein each R is the same or different and is a substituted or unsubstituted aryl group, and each Q is a sulfonate or carboxylate anion.

17. A method of preparing a photoresist composition and forming a photoresist relief image on a substrate comprising steps of:
(a) forming in a one-pot reaction a plurality of distinct aryl sulfonium photoactivable compounds wherein at least one of the compounds has the following formula I:

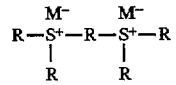

(I)

wherein each R is the same or different and is a substituted or unsubstituted aryl group, and each M is a counter anion,
(b) preparing a photoresist composition comprising admixing 1) a photoactive component that comprises the plurality of aryl sulfonium photoactivable compounds formed in step (a), and 2) a resin binder;
(c) applying the photoresist composition on a substrate;
(d) exposing the photoresist composition coating layer to patterned activating radiation and developing the exposed photoresist layer to provide a relief image.

18. The method of claim 17 wherein in step (a) the plurality of aryl sulfonium photoactivable compounds are formed by condensation of one or more triarylsulfonium halide compounds in the presence of acid.

19. The method of claim 17 wherein the photoactive component comprises one or more compounds of the following formulae (IV) and (V):

(IV)

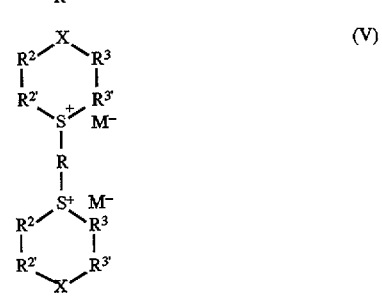

(V)

wherein each R is the same or different and is a substituted or unsubstituted aryl group; each $R^2$ and $R^{2'}$ are members of a first fused aryl ring; each $R^3$ and $R^{3'}$ are members of a second fused aryl ring; each X is independently a hetero atom, a $C_{1-3}$ alkylene, or a heterosubstituted $C_{1-3}$ alkylene; and each M is a counter anion.

20. The method of claim 17 wherein the substrate is a microelectronic wafer or a flat panel display substrate.

21. The method of claim 17 wherein the resin binder is a phenolic resin.

22. The method of claim 17 wherein the photoresist composition is a chemically-amplified positive-acting composition and the resin binder comprises acid labile groups.

23. The method of claim 17 wherein the photoresist composition is a negative-acting composition and comprises a cross-linking agent.

24. A method of preparing a photoresist composition and forming a photoresist relief image on a substrate comprising steps of:
(a) in a one-pot reaction condensing one or more triarylsulfonium compounds in the presence of acid to provide a plurality of different aryl sulfonium photoactivable compounds wherein at least one of the compounds has the following formula I:

(I)

wherein each R is the same or different and is a substituted or unsubstituted aryl group, and each M is a counter anion,
and wherein at least one of the plurality of aryl sulfonium photoactivable compounds is an aryl sulfonium compound that has a single cation;
(b) preparing a photoresist composition comprising admixing 1 ) a photoactive component that comprises a plurality of aryl sulfonium photoactivable compounds formed in step (a), and 2 ) a resin binder;
(c) applying the photoresist composition on a substrate;
(d) exposing the photoresist composition coating layer to patterned activating radiation and developing the exposed photoresist layer to provide a relief image.

* * * * *